United States Patent [19]
Slishman

[11] Patent Number: 5,899,854
[45] Date of Patent: May 4, 1999

[54] SPECULUM AND METHOD FOR INSERTING AN ELONGATED INSTRUMENT INTO AN ANIMAL'S BODY

[75] Inventor: Samuel H. Slishman, Albuquerque, N.M.

[73] Assignee: University of New Mexico, Albuquerque, N.M.

[21] Appl. No.: 09/062,701

[22] Filed: Apr. 20, 1998

[51] Int. Cl.⁶ ................................................. A61B 17/00
[52] U.S. Cl. .................................... 600/219; 600/201
[58] Field of Search ........................ 600/114, 184, 600/201, 208, 210, 213, 218, 219, 220, 221; 606/108, 190

[56] References Cited

U.S. PATENT DOCUMENTS

| | | | |
|---|---|---|---|
| 1,097,978 | 5/1914 | Johnson | 600/219 X |
| 3,653,388 | 4/1972 | Tenckhoff | |
| 3,893,454 | 7/1975 | Hagelin | 600/219 |
| 4,165,746 | 8/1979 | Burgin | 600/219 X |
| 4,608,982 | 9/1986 | Pollard | |
| 4,617,929 | 10/1986 | Gill | |
| 4,716,901 | 1/1988 | Jackson et al. | |
| 4,765,334 | 8/1988 | Weiss | |
| 5,183,464 | 2/1993 | Dubrul et al. | |
| 5,342,384 | 8/1994 | Sugarbaker | |
| 5,372,588 | 12/1994 | Farley et al. | |
| 5,667,514 | 9/1997 | Heller | |
| 5,681,265 | 10/1997 | Maeda et al. | 600/219 |
| 5,685,856 | 11/1997 | Lehrer | |
| 5,785,648 | 7/1998 | Min | 600/219 X |

FOREIGN PATENT DOCUMENTS

| | | | |
|---|---|---|---|
| 669511 | 8/1963 | Canada | 600/219 |
| 404336058 | 11/1992 | Japan | 600/220 |

*Primary Examiner*—Jeffrey A. Smith
*Attorney, Agent, or Firm*—Jagtiani & Associates

[57] ABSTRACT

The present invention provides a speculum having two half-beaks each linked to an elongated lever member. The speculum includes one or more pivot devices which cause the distal end of the two half-beaks to rotate away from each other when the proximal ends of the lever members are rotated towards each other. The present invention also provides a method for inserting an elongated instrument into an animal's body comprising the steps of: making an incision in an animal's skin; inserting a speculum having two half-beaks through the incision into the animal's body; opening the two half-beaks to permit an elongated instrument to be inserted therethrough; and inserting an elongated instrument through the two-half beaks and into the animal's body.

47 Claims, 3 Drawing Sheets

SPECULUM AND METHOD FOR INSERTING AN ELONGATED INSTRUMENT INTO AN ANIMAL'S BODY

BACKGROUND OF THE INVENTION

1. Field of the Invention

The present invention relates to a speculum for dilating the opening in an animal's body either for medical examination or to insert a medical instrument or tubing into the animal's body.

2. Description of the Prior Art

Existing methods for inserting a tube into an animal's body either involve using a blunt dissection method in which a clamp and the physician's fingers are used to insert the tube or involve using a trocar method in which a tube is guided over a sharp trocar. In the case of blunt dissection, multiple steps are required, including: incision, dissection, penetration into the lung cavity, probing with a finger, and then insertion of a tube using a clamp. In the case of using a trocar, this technique can be performed with one smooth step, but often damages tissue such as nerves, vessels or lung and is currently rarely used because of its high complication rate.

Therefore, there exists a need for a method for inserting a chest tube or other instrument into an animal's body which combines the lower risk of blunt dissection with the simplicity of a one step procedure.

SUMMARY OF THE INVENTION

It is therefore an object of the present invention to provide a speculum which can be used in a simple method for inserting a tube or other medical instrument safely into an animal's body.

It is another object of the present invention to provide a speculum which allows a medical professional to easily dilate an opening in an animal's body.

It is yet another object of the present invention to provide a speculum that can be easily maintained in an open position to allow a tube or other medical instrument to be inserted into an animal's body.

It is another object of the present invention to provide a speculum which has a blunt tip so that it does not lacerate blood vessels or internal organs when it is inserted into an animal's body yet can still be easily inserted into an animal's body.

The present invention provides a speculum having two half-beaks each linked to an elongated lever member. The speculum includes one or more pivot devices which cause the distal end of the two half-beaks to rotate away from each other when the proximal ends of the lever members are rotated towards each other.

The present invention also provides a method for inserting an elongated instrument into an animal's body comprising the steps of: making an incision in an animal's skin; inserting a speculum having two half-beaks through the incision into the animal's body; opening the two half-beaks to permit an elongated instrument to be inserted therethrough; and inserting an elongated instrument through the two-half beaks and into the animal's body.

Other objects and features of the present invention will be apparent from the following detailed description of the preferred embodiments.

BRIEF DESCRIPTION OF THE DRAWINGS

The invention will be described in conjunction with the accompanying drawings, in which.

DETAILED DESCRIPTION OF THE PREFERRED EMBODIMENTS

Definitions

For the purposes of the present invention the term "speculum" refers not only to medical instruments for dilating the opening of a body cavity, but to any device for dilating an opening. Although the speculum of the present invention is particularly useful in emergent surgical settings it may have other applications as well.

For the purposes of the present invention, the term "proximal" indicates the portion of a part of a speculum nearest to the end that a user grasps and the term "distal" indicates the portion of a part of a speculum furthest away from the end of a speculum that a user grasps.

Figure 3:
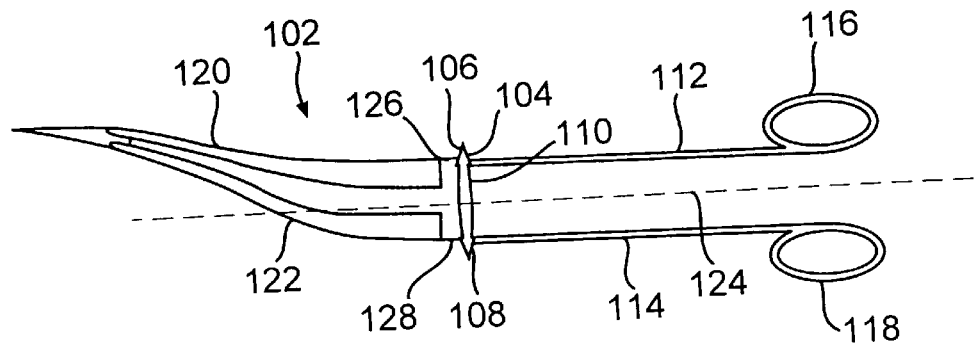
FIG. 3 is a side view of a second embodiment of a speculum made according to the present invention.

For the purposes of the present invention, the term "axial center" indicates either the line drawn between the pivot point about which the two half-beaks of a speculum of the present invention rotate and the pivot point about which the two lever members of the speculum rotate (for speculums in which the lever members rotate about a common pivot point, such as the speculum illustrated in FIGS. 1, 4, 5, 6 and 7) or the line drawn midway between the two pivot points about which the respective lever members rotate and midway between the lever members (for speculums in which the lever members each rotate about a respective pivot point, such as the speculum illustrated in FIG. 3).

For the purposes of the present invention, a part of a speculum is "axially straight" if it extends in a direction parallel to the axial center of the speculum.

For the purposes of the present invention, a part of a speculum is "axially curved: if it extends in a curve with respect to the axial center of the speculum.

For the purposes of the present invention, the term "elongated instrument" includes both flexible tubes, such as a chest tube; and stiff hollow tubes, such as a cannula or anethestic needle; stiff rods, such as a thermometer; flexible rods such as a fiber optic cable or fiber optic scope; gripping devices such as tweezers or forceps; various forms of clamps; and one or more of a medical professional's fingers.

Description

Figure 1:
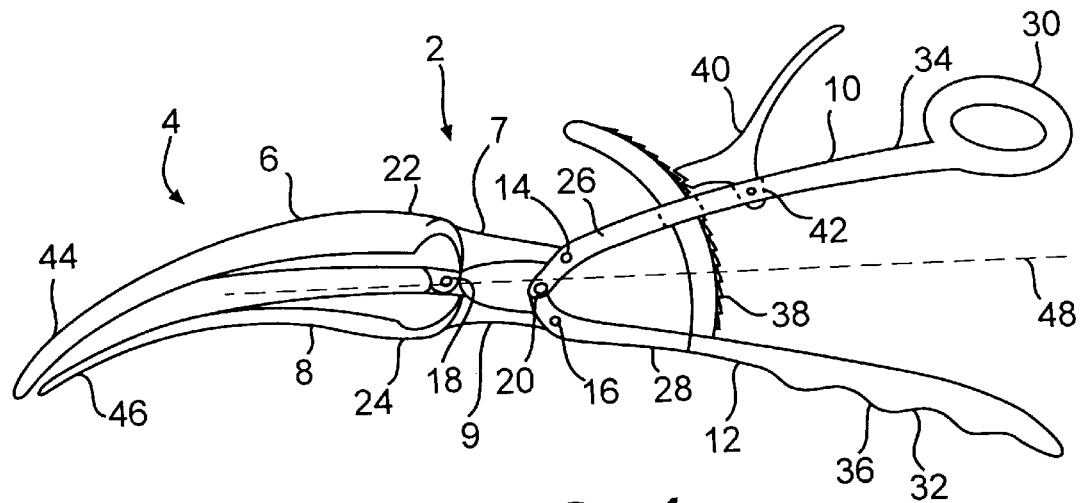
FIG. 1 is a side view of one embodiment of a speculum made according to the present invention.
Figure 2:
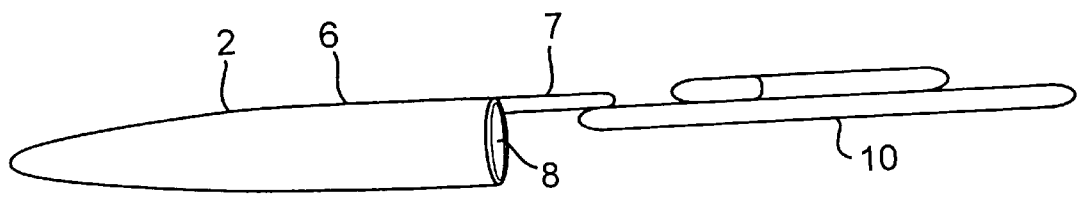
FIG. 2 is a top view of the speculum of FIG. 1.

FIGS. 1 and 2 illustrate a preferred embodiment of a speculum 2 made according to the present invention. The speculum 2 includes a beak 4 having two curved half-beaks 6 and 8. Half-beaks 6 and 8 include respective half-beak stems 7 and 9 which are rotatably linked to lever members 10 and 12, respectively, by means of respective linking pivots 14 and 16. Each of the linking pivots 14 and 16 may be one of the known types of linking pivots used in such devices as conventional speculums, scissors, barbecue tongs, etc. which both join two levers and allow the levers to rotate with respect to one another. Linking pivot may also removably fasten lever member 10 and 12 to half-beaks 6 and 8 at respective stems 7 and 9 so that beak 4 can be removed from lever members 10 and 12 for cleaning or so that a beak having a different size or shape can be mounted on lever members 10 and 12. The linking pivots 14 and 16 simultaneously join respective half-beaks 6 and 8 to lever members 10 and 12, respectively, while allowing each half-beak to rotate with respect to the lever member to which it is joined. Similar kinds of pivots can be used for a half-beak pivot 18 which rotatably links proximal ends 22 and 24 of respective half-beaks 6 and 8 to each other and for lever pivot 20 which rotatably links distal ends 26 and 28 of respective lever members 10 and 12 to each other.

Lever members 10 and 12 may include any conventional grasping device for allowing a user to grasp speculum 2, but preferably the grasping devices are a combination of finger loop 30 and crenellated grip 32 located at proximal ends 34 and 36 of lever members 10 and 12 as shown in FIG. 1. This combination of grasping devices allows a user to insert a thumb through finger loop 30 while grasping crenellated grip 32 with the remaining fingers of the hand. When a user grasps speculum 2 in this way and moves the proximal ends 34 and 36 towards each other, lever members 10 and 12 rotate about lever pivot 20 causing half-beaks 6 and 8, through linking pivots 14 and 16, to rotate around half-beak pivot 18 and, thereby, causing distal ends of 44 and 46 of respective half-beaks 6 and 8 to move away from each other so that beak 4 assumes a open position. The combination of pivots 14, 16, 18 and 20 constitute a "pivoting mechanism" that provides substantial mechanical advantage to a user, making it relatively easy for a user to open the beak 4 of speculum 2. Also, because lever members 10 and 12 are moved towards each other to open beak 4, the design of speculum 2 allows a user to employ his or her hand's flexor (grasping) muscles instead of the weaker extensor (ungrasping) muscles in opening the beak 4.

In an alternative embodiment of the present invention shown in FIG. 3, a speculum 102 includes a pivoting mechanism 104 which consists of two pivots 106 and 108 mounted on a crossing bar 110 which is extends across lever members 112 and 114. When finger loops 116 and 118 are moved together by a user, half-beaks 120 and 122 rotate away from each other. As shown in FIG. 3, half-beaks 120 and 122 are curved with respect to axial center 124 (shown by a dashed line) of speculum 102. In this embodiment, half-beak stems 126 and 128 are a part of lever members 112 and 114. Although the embodiment shown in FIG. 3 is simpler in construction than the speculum shown in FIG. 1, the pivoting mechanism 104 of speculum 102 does not provide as much mechanical advantage as the combination of pivots 14, 16, 18 and 20 provide a user of speculum 2 shown in FIG. 1.

Figure 4:
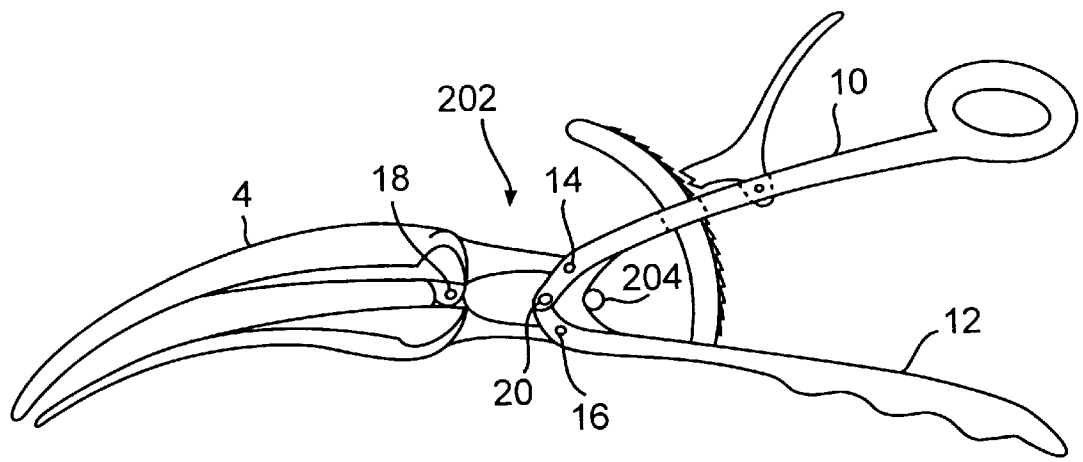
FIG. 4 is a side view of a third embodiment of a speculum made according to the present invention.
Figure 5:
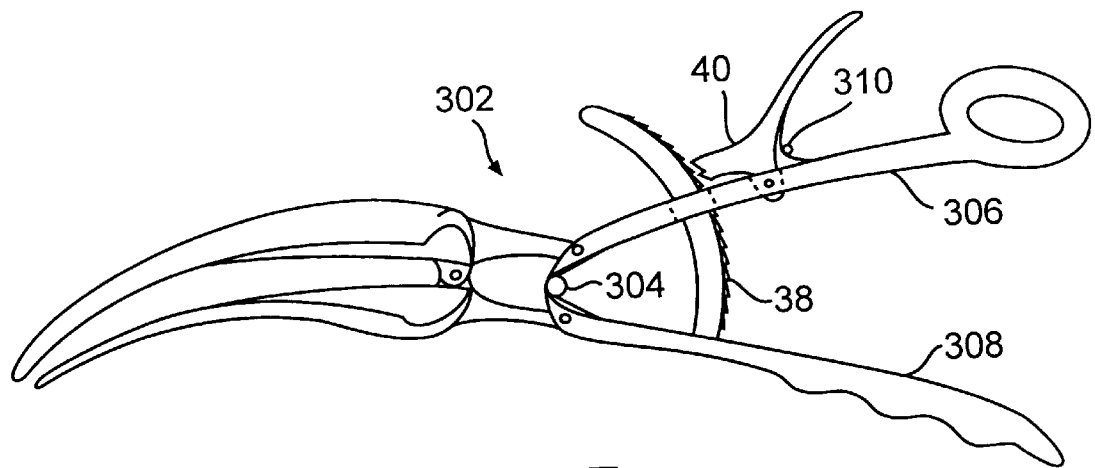
FIG. 5 is a side view of a fourth embodiment of a speculum made according to the present invention.

Other pivoting mechanisms employing springs can also be used with the present invention as shown by the embodiments illustrated in FIGS. 4 and 5. FIG. 4 shows a speculum 202 of the present invention in which the pivoting mechanism includes not only pivots 14, 16, 18 and 20, but a control spring 204 which is attached to lever members 10 and 12. Control spring 204 gives a user increased control over how much beak 4 opens, because spring 204 provides increased resistance as lever members 10 and 12 are squeezed closer to each other and beak 4 opens wider. Control 204 also maintains beak 4 in a closed position when lever members 10 and 12 are not squeezed by a user.

FIG. 5 shows a speculum 302 made according to the present invention in which lever pivot 20 has been replaced by a pivot spring 304. In addition to acting as a pivot for lever members 306 and 308, pivot spring 304 also provides a control function similar to that of control spring 204 shown in FIG. 4. Although only a few specific pivoting mechanisms have been shown in the embodiments shown in the drawing figures, the pivoting mechanism of the speculum of the present invention can employ various types and combinations of conventional pivots and springs which cause the beak to open when the lever members are squeezed towards each other.

Beak 4 may be maintained in an open position in a number of ways. For example, as shown in FIG. 1, a ratchet 38 may be attached to lever member 12 and a pawl 40 rotatably attached to lever member 10 by means of a conventional pawl pivot 42, which may be of the same type as pivots 14, 16, 18 and 20. Pawl pivot 42 may be made in such a way that it does not freely rotate but instead is restricted from free rotation so that some force must be applied to pawl 40 before pawl 40 will rotate about pawl pivot 42, so that pawl 40 will stay in place on ratchet 38 without the user holding pawl 40 in place. Such "restricted" pivots are well known in the art and have been used in such devices as pliers and gardening shears. In order to allow beak 4 to open, the user releases pawl 40 from engagement with ratchet 38 and the user squeezes the proximal ends 34 and 36 of lever members 10 and 12 together. In order to fix beak 4 in a desired open position, the user re-engages pawl 40 with ratchet 38.

FIG. 5 shows an alternative ratchet and pawl combination that can be used with the present invention. In this embodiment, a bent pawl spring 310 is attached to pawl 40 and lever member 10 and urges pawl 40 into engagement with ratchet 38. In order to open beak 4, a user must first release pawl 40 from engagement with ratchet 38. When beak 4 has been opened a desired amount, the user releases pawl 40 and pawl 40 springs back to re-engage ratchet 38.

Although in a preferred embodiment, the devices which are used to maintain beak 4 in a open position are a ratchet 38 and pawl 40 which allow beak 4 to be maintained in a variety of open positions, other devices could be used which only allow the beak 4 to be in one or just a few open positions. For example, a ratchet could be mounted on one of the lever members which only includes one tooth for engaging a pawl mounted on the other lever member. Other known devices for maintaining a pair of joined lever members in a particular position could also be used, such as the latch mechanisms similar to the type used to keep toenail clippers and garden shears in closed positions.

Figure 8:
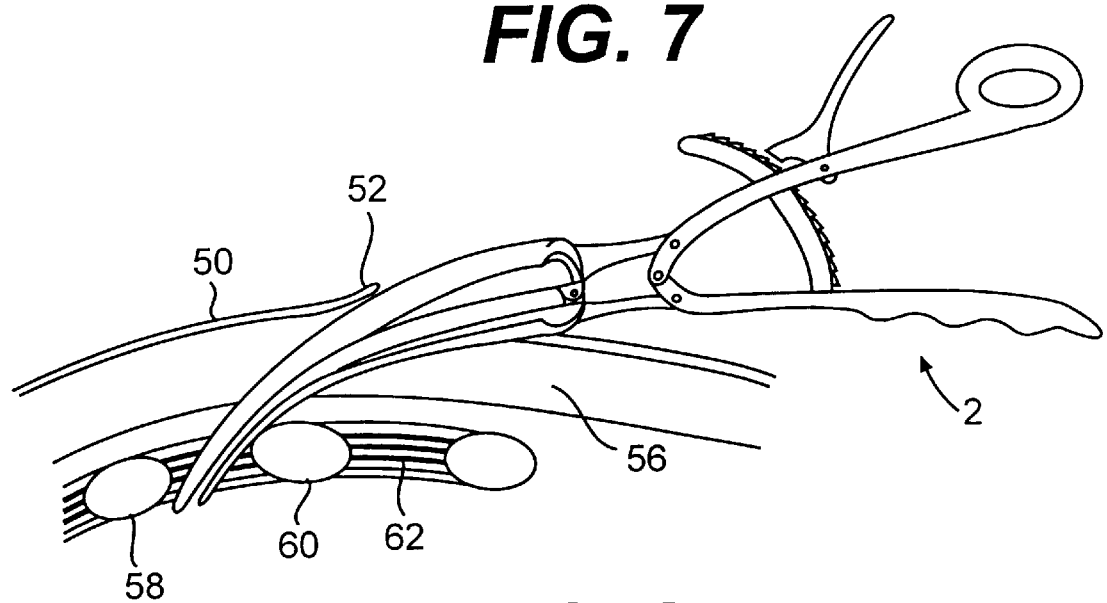
FIG. 8 is an illustration of the speculum of FIG. 1 being inserted into the body of a patient.
Figure 9:
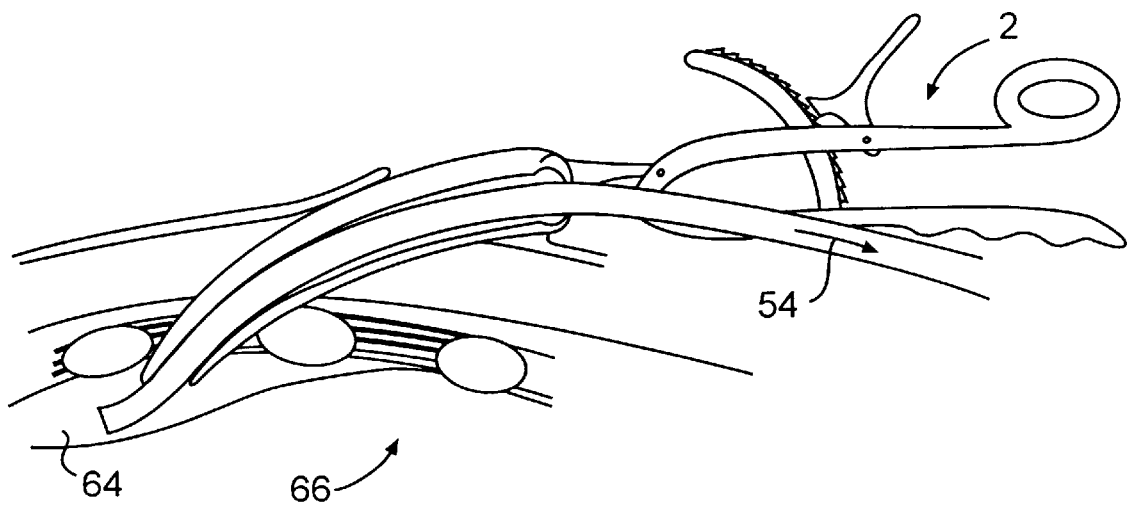
FIG. 9 is an illustration of the speculum of FIG. 8 showing a tube being inserted through the speculum and into the patient.

With respect to the half-beaks 6 and 8, preferably they have parabolic shape in profile as shown in FIG. 2 (half-beak 8 is obscured in this drawing). This "blunt tipped" shape prevents half-beaks 6 and 8 from puncturing or cutting tissue when they are inserted inside a patient. However, the shape of half-beaks 6 and 8 is effective in allowing beak 4 to effectively spread tissue fibers that the beak 4 passes through. Half-beaks 6 and 8, are also axially curved and have respective half-beak distal ends 44 and 46 which are displaced to one side with respect to axial center 48 (shown by dashed line in FIG. 1) of speculum 2. This curving of half beaks 6 and 8 and displacement of their distal ends 44 and 46 in this way allows beak 4, when beak 4 is in a closed position, to be more easily inserted into a human body 50 through an incision in the skin 52 as shown in FIG. 8. Once beak 4 is inserted in a body 50, the beak 4 can be opened as described above so that a flexible chest tube 54 can be inserted between and through half-beaks 6 and 8 as shown in FIG. 9. To allow a tube to be more easily inserted through half-beaks 6 and 8, half-beaks 6 and 8 are not only curved in an axial direction but are also curved in cross-section as shown in FIGS. 1, 8 and 9. Once tube 54 is in place, the speculum 2 can be removed.

As opposed to a hollow chest tube, it is possible to insert other types of elongated instruments such as a fiber optic scope through half-beaks 6 and 8 and into the body. When a fiber optic scope is inserted through the tool, the speculum provides direct visual access to the pleural cavity and the lung.

Other "elongated instruments" which may be inserted through the half-beaks of the speculum of the present invention include one or more of a physician's fingers, clamps, tweezers, and forceps depending on the medical operation performed. For example one or more of a physician's fingers can be inserted through the beak to probe inside a patient's body or to retrieve a foreign object. Gripping devices such as a tweezers or forceps can also be inserted through the half-beaks to retrieve a foreign object such as metal or wood fragments from a patient's body. The speculum of the present invention may also be used to place surgical clamps within a body. For many of these elongated instruments, it may be desirable to use a speculum having a straight beak such as speculum 402 shown in FIG. 6.

The speculum 2 can be used in relatively tight spaces in a human body. For example, as shown in FIGS. 8 and 9, beak 4 may be inserted through an incision in the skin 52, through a layer of fat 56, in between two ribs 58 and 60, through intercostal muscles 62, and into the pleural space 64 surrounding a lung 66. The speculum 2 allows for rapid placement of the chest tube 54 with one step after skin incision.

The speculum of the present invention may be made of any suitable material such as metal or plastic or a combination of metal and plastic.

Figure 6:
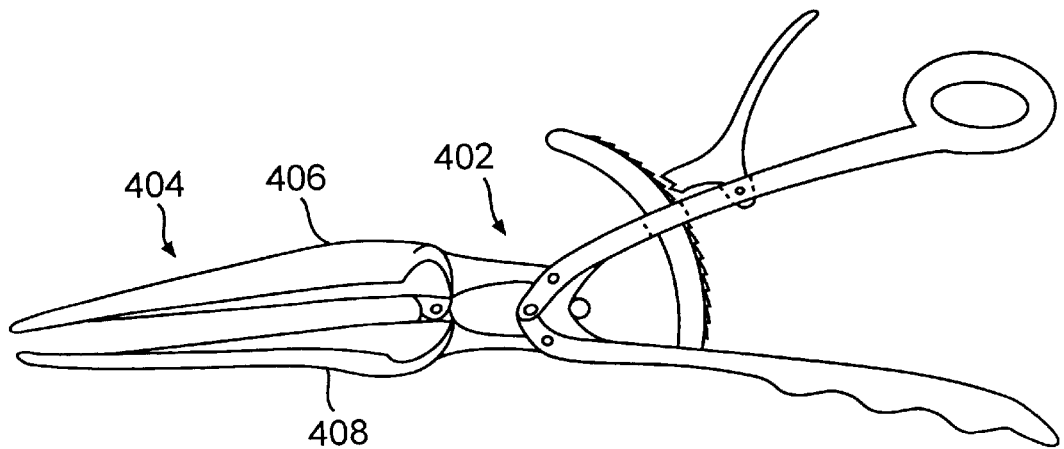
FIG. 6 is a side view of a fifth embodiment of a speculum made according to the present invention.

Although in the embodiment shown in FIGS. 1 through 5, the half-beaks of the present invention are axially curved, there may be certain circumstances where it is preferable that half-beaks be axially straight, such as when a stiff cannula or anesthetic needle is to be inserted through the half-beaks. FIG. 6 illustrates such an embodiment in which a speculum 402 of the present invention has a beak 404 comprised to two half-beaks 406 and 408 which are axially straight.

Figure 7:
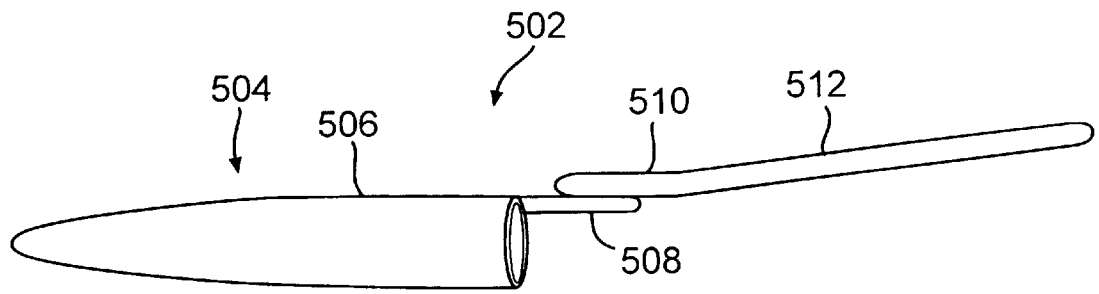
FIG. 7 is a side view of a sixth embodiment of a speculum made according to the present invention.

As shown in FIG. 2, lever members 10 and 12 may be mounted to the left of half-beak stems 7 and 9, respectively (when viewed from above; lever member 12 and beak stem 9 are hidden behind lever member 10 and beak stem 7 in this view). However, as illustrated in the embodiment shown in FIG. 7 a speculum 502 of the present invention may have lever members which are mounted to the right of half-beak stems (when viewed from above) of respective half-beaks so that the levers do not interfere with an elongated instrument (not shown) inserted through beak 504. In FIG. 7, only the top half-beak 506, top half-beak stem 508, and top lever member 510 are visible. To further reduce interference between the lever members in this embodiment and an elongated instrument inserted through beak 504, respective proximal ends of the lever members are to be bent away from beak 504 as shown in FIG. 7 (the bottom lever member, including its bent proximal end 512, is hidden behind top lever member 510 in this view). As in the embodiment shown in FIG. 1, in FIG. 7 beak 504 of speculum 502 may be removably mounted on the lever members so that the beak 504 can be removed for cleaning or replaced with a beak having a different size or shape, such as the straight beak 404 shown in FIG. 6.

The speculum of the present invention also limits bloody wastes, is easily autoclaved and can be made reusable. It has very few parts where blood can collect. Furthermore, the portion of the speculum that enters the body can be made especially smooth and easy to clean.

The method of the present invention allows for a simplified method for inserting a chest tube in a patient. Currently, a "chest tube tray" is necessary to hold the numerous implements required for chest tube insertion. In contrast, the method of the present invention only requires the additional aid of a scalpel for an initial skin incision. Because of the simplicity of the method of the present invention, it could be used to make the placement of chest tubes a possible procedure for EMS (emergency medical services) crews in the field or in "back-country" settings or acute settings where time is precious such as in trauma rooms.

When a speculum having a curved beak is used in the method of the present invention, the method of the present invention allows a curved track to be tunneled through tissue. This path provides for the creation of an airtight seal around a chest tube inserted using the present invention's speculum after the speculum is removed.

Although the speculum and method of the present invention have been primarily discussed in connection with their use in a patient's pleural cavity, it should be apparent that they can be used in other parts of the body such as in the region of the heart, abdomen, arms, legs, etc.

Although the present invention has been fully described in conjunction with the preferred embodiment thereof, it is to be understood that various changes and modifications may be apparent to those skilled in the art. Such changes and modifications are to be understood as included within the scope of the present invention as defined by the appended claims, unless they depart therefrom.

What is claimed is:

1. A speculum comprising:
   a beak including two half-beaks, each of said half-beaks having a distal end and a proximal end;
   two elongated lever members, each of said lever members being attached to a respective one of said half-beaks, each of said lever members having a distal end and a proximal end; and
   pivot means connected to said half-beaks and said lever members for rotating said distal ends of said half-beaks away from each other when said proximal ends of said lever members are rotated towards each other, said pivot means comprising: a half-beak pivot which rotatably links said half-beaks; a lever pivot which rotatably links said lever members; and two linking pivots, each of said linking pivots rotatably linking one of said lever members to a respective one of said half-beaks.

2. The speculum of claim 1, further comprising a control spring attached to said lever members and providing a positive resistance to said lever members being rotated towards each other.

3. The speculum of claim 1, wherein said speculum further comprises a position maintaining means for maintaining said half-beaks in an open position.

4. The speculum of claim 3, wherein said position maintaining means comprises a ratchet member and a pawl for engaging said ratchet member.

5. The speculum of claim 3, wherein said position maintaining means comprises a curved ratchet member attached to one of said lever members and a pawl rotatably attached to the other of said lever members for engaging said ratchet member.

6. The speculum of claim 5, wherein said position maintaining means further comprises a spring means for urging said pawl into engagement with said ratchet member.

7. The speculum of claim 1, wherein each of said half-beaks has a parabolic shape.

8. The speculum of claim 1, wherein each of said half-beaks is curved in cross-section for permitting an elongated instrument to be inserted through an opening between said half-beaks when said half-beaks are in an open position.

9. The speculum of claim 1, wherein each of said half-beaks has a parabolic shape and each of said half-beaks is curved in cross-section for permitting an elongated instrument to be inserted through an opening between said half-beaks when said half-beaks are in an open position.

10. The speculum of claim 9, wherein each said distal end of each of said half-beaks is axially curved and said distal ends of said half-beaks are displaced to one side of the axial center of said speculum.

11. The speculum of claim 1, wherein each said distal end of each of said half-beaks is axially curved and said distal ends of said half-beaks are displaced to one side of the axial center of said speculum.

12. The speculum of claim 1, wherein said half-beaks are axially straight.

13. The speculum of claim 1, wherein each of said distal ends of said half-beaks is blunt.

14. The speculum of claim 1, wherein said half-beaks are removably attached to said lever members.

15. The speculum of claim 1, said proximal ends of said lever members are bent.

16. A speculum comprising:
    a beak including two half-beaks, each of said half-beaks having a distal end and a proximal end;
    two elongated lever members, each of said lever members being attached to a respective one of said half-beaks, each of said lever members having a distal end and a proximal end; and
    pivot means connected to said half-beaks and said lever members for rotating said distal ends of said half-beaks away from each other when said proximal ends of said lever members are rotated towards each other, said pivot means comprising: a half-beak pivot which rotatably links said half-beaks; a lever spring which links said lever members and which provides a positive resistance to said lever members being rotated towards each other; and two linking pivots, each of said linking pivots rotatably linking one of said lever members to a respective one of said half-beaks.

17. The speculum of claim 16, wherein said speculum further comprises a position maintaining means for maintaining said half-beaks in an open position.

18. The speculum of claim 17, wherein said position maintaining means comprises a ratchet member and a pawl for engaging said ratchet member.

19. The speculum of claim 17, wherein said position maintaining means comprises a curved ratchet member attached to one of said lever members and a pawl rotatably attached to the other of said lever members for engaging said ratchet member.

20. The speculum of claim 19, wherein said position maintaining means further comprises a spring means for urging said pawl into engagement with said ratchet member.

21. The speculum of claim 16, wherein each of said half-beaks has a parabolic shape.

22. The speculum of claim 16, wherein each of said half-beaks is curved in cross-section for permitting an elongated instrument to be inserted through an opening between said half-beaks when said half-beaks are in an open position.

23. The speculum of claim 16, wherein each of said half-beaks has a parabolic shape and each of said half-beaks is curved in cross-section for permitting an elongated instrument to be inserted through an opening between said half-beaks when said half-beaks are in an open position.

24. The speculum of claim 23, wherein each said distal end of each of said half-beaks is axially curved and said distal ends of said half-beaks are displaced to one side of the axial center of said speculum.

25. The speculum of claim 16, wherein each said distal end of each of said half-beaks is axially curved and said distal ends of said half-beaks are displaced to one side of the axial center of said speculum.

26. The speculum of claim 16, wherein said half-beaks are axially straight.

27. The speculum of claim 16, wherein each of said distal ends of said half-beaks is blunt.

28. The speculum of claim 16, wherein said half-beaks are removably attached to said lever members.

29. The speculum of claim 16, said proximal ends of said lever members are bent.

30. A speculum comprising:
    a beak including two half-beaks, each of said half-beaks having a distal end and a proximal end;
    two elongated lever members, each of said lever members being attached to a respective one of said half-beaks, each of said lever members having a distal end and a proximal end; and
    pivot means connected to said half-beaks and said lever members for rotating said distal ends of said half-beaks away from each other when said proximal ends of said lever members are rotated towards each other, said pivot means comprising: a crossing member extending across said lever members and including two pivots, each of said pivots being rotatably linked to a respective one of said lever members.

31. The speculum of claim 30, further comprising a control spring attached to said lever members and providing a positive resistance to said lever members being rotated towards each other.

32. The speculum of claim 30, wherein said speculum further comprises a position maintaining means for maintaining said half-beaks in an open position.

33. The speculum of claim 32, wherein said position maintaining means comprises a ratchet member and a pawl for engaging said ratchet member.

34. The speculum of claim 32, wherein said position maintaining means comprises a curved ratchet member attached to one of said lever members and a pawl rotatably attached to the other of said lever members for engaging said ratchet member.

35. The speculum of claim 34, wherein said position maintaining means further comprises a spring means for urging said pawl into engagement with said ratchet member.

36. The speculum of claim 30, wherein each of said half-beaks has a parabolic shape.

37. The speculum of claim 30, wherein each of said half-beaks is curved in cross-section for permitting an elongated instrument to be inserted through an opening between said half-beaks when said half-beaks are in an open position.

38. The speculum of claim 30, wherein each of said half-beaks has a parabolic shape and each of said half-beaks is curved in cross-section for permitting an elongated instrument to be inserted through an opening between said half-beaks when said half-beaks are in an open position.

39. The speculum of claim 38, wherein each said distal end of each of said half-beaks is axially curved and said distal ends of said half-beaks are displaced to one side of the axial center of said speculum.

40. The speculum of claim 30, wherein each said distal end of each of said half-beaks is axially curved and said distal ends of said half-beaks are displaced to one side of the axial center of said speculum.

41. The speculum of claim 30, wherein said half-beaks are axially straight.

42. The speculum of claim 30, wherein each of said distal ends of said half-beaks is blunt.

43. The speculum of claim 30, wherein said half-beaks are removably attached to said lever members.

44. The speculum of claim 30, said proximal ends of said lever members are bent.

45. A method for inserting an elongated instrument into an animal's body comprising the steps of:

making an incision in an animal's skin;

inserting a speculum through the incision into the animal's body, said speculum comprising:
　　a beak including two half-beaks, each of said half-beaks having a distal end and a proximal end;
　　two elongated lever members, each of said lever members being attached to a respective one of said half-beaks, each of said lever members having a distal end and a proximal end; and
　　pivot means connected to said half-beaks and said lever members for rotating said distal ends of said half-beaks away from each other when said proximal ends of said lever members are rotated towards each other, said pivot means comprising: a half-beak pivot which rotatably links said half-beaks; a lever pivot which rotatably links said lever members; and two linking pivots, each of said linking pivots rotatably linking one of said lever members to a respective one of said half-beaks;

opening said half-beaks to permit an elongated instrument to be inserted therethrough; and inserting an elongated instrument through said-half beaks and into the animal's body.

46. A method for inserting an elongated instrument into an animal's body comprising the steps of:

making an incision in an animal's skin;

inserting a speculum through the incision into the animal's body, said speculum comprising:
　　a beak including two half-beaks, each of said half-beaks having a distal end and a proximal end;
　　two elongated lever members, each of said lever members being attached to a respective one of said half-beaks, each of said lever members having a distal end and a proximal end; and
　　pivot means connected to said half-beaks and said lever members for rotating said distal ends of said half-beaks away from each other when said proximal ends of said lever members are rotated towards each other, said pivot means comprising: a half-beak pivot which rotatably links said half-beaks; a lever spring which links said lever members and which provides a positive resistance to said lever members being rotated towards each other; and two linking pivots, each of said linking pivots rotatably linking one of said lever members to a respective one of said half-beaks;

opening said half-beaks to permit an elongated instrument to be inserted therethrough; and inserting an elongated instrument through said-half beaks and into the animal's body.

47. A method for inserting an elongated instrument into an animal's body comprising the steps of:

making an incision in an animal's skin;

inserting a speculum through the incision into the animal's body, said speculum comprising:
　　a beak including two half-beaks, each of said half-beaks having a distal end and a proximal end;
　　two elongated lever members, each of said lever members being attached to a respective one of said half-beaks, each of said lever members having a distal end and a proximal end; and
　　pivot means connected to said half-beaks and said lever members for rotating said distal ends of said half-beaks away from each other when said proximal ends of said lever members are rotated towards each other, said pivot means comprising: a crossing member extending across said lever members and including two pivots, each of said pivots being rotatably linked to a respective one of said lever members;

opening said half-beaks to permit an elongated instrument to be inserted therethrough; and inserting an elongated instrument through said-half beaks and into the animal's body.

* * * * *